US009102785B2

(12) United States Patent
Martz et al.

(10) Patent No.: US 9,102,785 B2
(45) Date of Patent: Aug. 11, 2015

(54) CURABLE COMPOSITIONS BASED ON POLYURETIDIONES, POLYTHIOLS AND PHOTOACTIVABLE BASES AND GENERATION OF ISOCYANATES FROM URETIDIONES

(75) Inventors: Jonathan T. Martz, Glenshaw, PA (US); Deborah E. Hayes, Verona, PA (US); Debra L. Singer, Wexford, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 1596 days.

(21) Appl. No.: 12/411,429

(22) Filed: Mar. 26, 2009

(65) Prior Publication Data

US 2009/0258962 A1    Oct. 15, 2009

Related U.S. Application Data

(60) Provisional application No. 61/044,203, filed on Apr. 11, 2008, provisional application No. 61/044,207, filed on Apr. 11, 2008.

(51) Int. Cl.
*C08G 18/79* (2006.01)
*C08G 18/20* (2006.01)
*C08G 18/38* (2006.01)
*C09D 175/04* (2006.01)

(52) U.S. Cl.
CPC .......... *C08G 18/798* (2013.01); *C08G 18/2063* (2013.01); *C08G 18/3876* (2013.01); *C09D 175/04* (2013.01)

(58) Field of Classification Search
CPC ............. C08G 18/798; C08G 18/2063; C08G 18/3876; C09D 175/04

USPC ....................... 522/53, 134, 46, 45
See application file for complete search history.

(56) References Cited

U.S. PATENT DOCUMENTS

| 4,413,079 A | 11/1983 | Disteldorf et al. ............ 524/169 |
| 4,463,154 A | 7/1984 | Disteldorf et al. .............. 528/45 |
| 5,814,689 A * | 9/1998 | Goldstein et al. ............... 524/86 |
| 6,531,188 B1 | 3/2003 | Maag et al. .................... 427/492 |
| 6,867,244 B2 | 3/2005 | Klinkenberg et al. ........ 522/174 |
| 2005/0209361 A1 | 9/2005 | Detrembleur et al. ........ 522/183 |
| 2005/0209427 A1 | 9/2005 | Detrembleur et al. .......... 528/44 |

FOREIGN PATENT DOCUMENTS

| WO | WO 00/39186 A1 | 7/2000 |
| WO | WO 2008/037635 A1 | 4/2008 |

OTHER PUBLICATIONS

"Polyisocyanates," European Aliphatic Isocyanates Producers Association.; ALIPA-HSE & Polyisocyanates.*
K. Dietliker et al., "Advancements in photoinitiators—Opening up new applications for radiation curing", Progress in Organic Coatings 58(2007), pp. 146-157.

* cited by examiner

*Primary Examiner* — Mark Eashoo
*Assistant Examiner* — Jessica Roswell
(74) *Attorney, Agent, or Firm* — William J. Uhl

(57) ABSTRACT

Curable compositions based on polyuretidiones, polythiols and photoactivable bases are disclosed. Also a process for generating isocyanate groups by exposing uretidiones to radiation in the range of 100-315 nm is disclosed. The process can be used in a dual curing system for curing compositions that comprise groups that undergo photoinduced polymerizations and active hydrogen groups that react with the generated isocyanates.

19 Claims, No Drawings

CURABLE COMPOSITIONS BASED ON POLYURETIDIONES, POLYTHIOLS AND PHOTOACTIVABLE BASES AND GENERATION OF ISOCYANATES FROM URETIDIONES

CROSS-REFERENCE TO A RELATED APPLICATION

This application claims the benefit of U.S. Provisional Patent Application Ser. No. 61/044,203 filed Apr. 11, 2008, and entitled: "CURABLE COMPOSITIONS BASED ON POLYURETIDIONES, POLYTHIOLS AND PHOTOACTIVABLE BASES", and U.S. Provisional Patent Application Ser. No. 61/044,207 filed Apr. 11, 2008, and entitled: "GENERATION OF ISOCYANATES FROM URETIDIONES".

FIELD OF THE INVENTION

The present invention relates to curable compositions particularly compositions that are curable at ambient temperature and that are useful as decorative and protective coatings.

The present invention also relates to the generation of isocyanates from uretidiones by exposing the uretidiones to ultraviolet radiation. The invention also relates to a dual cure process for curing compositions that contain uretidione groups and groups that undergo photoinduced radical polymerization and/or cationic polymerization.

BACKGROUND OF THE INVENTION

Polyuretidiones are well known as curing agents for hydroxyl functional polymers. Polyuretidiones are typically prepared by dimerizing a polyisocyanate to form a uretidione with unreacted isocyanate groups which can then be extended with a polyol to form a polymeric material containing two or more uretidione groups in the polymer chain. Typically the polymer has little if any free isocyanate groups, which is achieved by controlling the stoichiometry of the polyisocyanate, polyol and the use of blocking agent. When combined with hydroxyl-functional polymers the resulting composition can be heated to produce a cured composition. In the curing reaction the uretidione groups disassociate giving isocyanate groups that react with the hydroxyl groups. Although the polyuretidiones are desirable from the perspective that they avoid the handling problems associated with polyisocyanates while still providing for a urethane cure, relatively high temperatures on the order of 150° C. are needed for a complete cure.

It has been found that replacing polyols with polythiols and using a suitable catalyst results in ambient temperature cure compositions. Unfortunately, the pot life of the compositions is very poor.

SUMMARY OF THE INVENTION

The present invention provides a curable composition comprising:
a) a polyuretidione
b) a polythiol and
c) a photoactivable nitrogen base The above mentioned ingredients can be combined in a one package system in which the ingredients are essentially unreactive. The composition can be applied as a coating and exposed to ultraviolet (UV) light, which brings about rapid and complete cure. The UV radiation releases a nitrogen containing base that catalyzes the curing reaction.

The present invention also resides in the unexpected discovery that uretidiones that are essentially free of isocyanate functionality when exposed to ultraviolet radiation in the 100-315 nm region generate free isocyanate functionality. The invention can be used to provide a unique dual curing system involving a composition comprising groups
 i that undergo photoinduced free radical polymerization or photoinduced cationic polymerization,
 ii at least one uretidione group,
 iii at least one active hydrogen group.

The compositions upon exposure to ultraviolet radiation in the range 100 to 315 nanometers (nm) result in the polymerization of the groups (i) above and also generate isocyanate groups from the uretidione group which react with the active hydrogen groups resulting in a cured composition.

DETAILED DESCRIPTION OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

The term "polymer" is also meant to include copolymer and oligomer.

Acrylic and methacrylic are designated as (meth)acrylic.

Aliphatic and cycloaliphatic are designated as (cyclo)aliphatic.

The term "radiation" means free radical generating radiation in the range of 100 to 315 nm.

The term "photoactivable base" means a compound that contains a moiety that absorbs UV radiation, particularly in the 100-650 nanometer (nm) region and dissociates to give a primary, secondary or tertiary amine, preferably an amidine base.

The uretidiones are obtained by catalytic dimerization of polyisocyanates by methods which are known in the art.

Examples of suitable polyisocyanates a (cyclo)aliphatic and aromatic polyisocyanates, such as diisocyanates, including 1,4-diisocyanatobutane, 1,6-diisocyanatohexane (HDI), trimethylhexane diisocyanate, 1,3- and 1,4-bisisocyanatomethylcyclohexane, isophorone diisocyanate (IPDI), 4,4'-diisocyanatodicyclohexylmethanes, 1,3- and 1,4-xylylene diisocyanates (XDI), diphenylmethane 4,4'-diisocyanate and diphenylmethane 2,4'-diisocyanate (MDI), 2,4- and 2,6-toluene diisocyanate (TDI), or mixtures thereof. HDI and IPDI are preferred.

Examples of dimerization catalysts are: trialkylphosphines, amino substituted phosphines and amino substituted pyridines such as dimethylaminopyridines, and tris(dimethylamino)phosphine.

The result of the dimerization reaction depends, in a manner known to the skilled person, on the catalyst used, on the process conditions and on the polyisocyanates employed. In particular it is possible for products to be formed which contain on average more than one uretidione group per molecule, the number of uretidione groups being subject to a distribution.

Preferred uretidione compounds are prepared from the catalytic dimerization of HDI and IDPI.

The uretidiones are NCO-functional compounds and may be used directly or they can also be subjected to further reaction. This further reaction may be, for example, blocking of the free NCO groups or further reaction of NCO groups with NCO-reactive compounds having a functionality of 2 or more to extend the uretidiones to form polyuretidiones. This gives compounds containing uretdione groups and of higher molecular weight, which, depending on the chosen proportions, may also contain NCO groups or may be free from NCO groups or may contain isocyanate groups that are blocked.

Blocking agents suitable for example are alcohols, lactams, oximes, malonates, alkyl acetoacetates, triazoles, phenols, imidazoles, pyrazoles and amines, such as butanone oxime, diisopropylamine, 1,2,4-triazole, dimethyl-1,2,4-triazole, imidazole, diethyl malonate, ethyl acetoacetate, acetone oxime, 3,5-dimethylpyrazole, epsilon.-caprolactam, N-tert-butylbenzylamine, cyclopentanone carboxyethyl ester or any desired mixtures of these blocking agents.

Example of NCO-reactive compounds with a functionality of two or more are polyols with a functionality of two or more, such as ethylene glycol, propane-1,2-diol, propane-1,3-diol, diethylene glycol, dipropylene glycol, the isomeric butanediols, neopentyl glycol, hexane-1,6-diol, 2-ethylhexanediol and tripropylene glycol or else alkoxylated derivatives of these alcohols. Suitable trihydric alcohols are glycerol or trimethylolpropane or their alkoxylated derivatives. Tetrahydric alcohols are pentaerythritol or its alkoxylated derivatives.

The resulting polyuretidione typically contains at least 2, such as from 3 to 10 uretidione groups. More typically the polyuretidione contains from 5 to 45% by weight of uretidione groups; 10 to 55% by weight urethane groups; and less than 2% by weight isocyanate groups; the percentages by weight being based on total weight of uretidione, urethane and isocyanate groups.

For dual curing compositions the NCO-functional uretidiones or polyuretidiones as described above can be further reacted with an active hydrogen-containing compound that contains groups that undergo photoinduced free radical polymerization or photoinduced cationic polymerization when exposed to UV radiation in the 100-315 nm range. Such groups are for example acrylic, methacrylic, vinyl ether and epoxy groups.

Examples of such active hydrogen-containing compounds are hydroxyl-containing compounds such as 2-hydroxyethyl (meth)acrylate, polyethylene oxide mono(meth)acrylate, polypropylene oxide mono(meth)acrylate, 2-hydroxypropyl (meth)acrylate, 4-hydroxybutyl(meth)acrylate, hydroxybutyl vinyl ether, 3-hydroxy-2,2-dimethylpropyl(meth)acrylate. Other examples include the hydroxy-functional mono-, di- or where possible higher acrylates of higher functionality polyols such as, for example, glyceryl di(meth)acrylate, trimethylolpropane di(meth)acrylate, pentaerythritol tri(meth)acrylate and dipentaerythritol penta(meth)acrylate. Also hydroxyl compounds that contain groups that undergo photoinduced cationic polymerization such as glycidol can be used.

Besides being integral with the uretidione or polyuretidione molecule, the group that undergoes photoinduced free radical or photoinduced cationic polymerization can be present as a separate component. Such materials are well known in the art.

Suitable photoinduced free radically polymerizable compounds and polymers include compounds and polymers containing photoinduced polymerizable ethylenic unsaturation. Examples of suitable polymers are polyurethane acrylates, polyester acrylates, polyether acrylates, polyacrylates derived from polyepoxides, acrylate functional acrylic polymers, unsaturated polyesters, and polyvinyl ethers. The polyurethane acrylates, polyester acrylates, polyacrylates derived from polyepoxides, and acrylate functional acrylic polymers can be prepared from polyurethane polyols, polyester polyols, polyether polyols, polybutadiene polyols, acrylic polyols, and epoxide resins by reacting all or portions of the hydroxyl groups or epoxy groups with acrylic acid. Suitable photoinduced free radically polymerizable compounds can be formed from monomeric polyols like pentaerythritol and trimethylol propane, propylene glycol, and ethylene glycol, which can be reacted with (meth)acrylic acid.

Suitable cationically polymerizable polymers and compounds include epoxy resins and vinyl ethers.

Suitable epoxy resins are well known in the art. Suitable epoxy resins include polyepoxides in which the resin contains at least two epoxide groups per molecule. The polyepoxides may be saturated or unsaturated, cyclic or acyclic, aliphatic, alicyclic, aromatic, or heterocyclic. The polyepoxides can contain substituents such as halogens, hydroxyl groups, and ether groups.

Other suitable epoxy resins include glycidyl ethers, glycidyl esters, glycidyl amines, linear-aliphatic epoxides and alicyclic epoxides, and modified epoxy resins derived therefrom. For example, glycidyl ethers of polyhydric phenols, polyglycidyl ethers of polyhydric alcohols, and polyglycidyl esters of polycarboxylic acids can be used in the present invention.

Examples of glycidyl ethers of polyhydric phenols include bisphenol A and bisphenol F. The glycidyl ethers of polyhydric phenols can be obtained by reacting epichlorohydrin and bisphenols.

Polyglycidyl ethers of polyhydric alcohol can be derived from polyhydric alcohols like ethylene glycol, propylene glycol, butylene glycol, 1,6-hexylene glycol, neopentyl glycol, diethylene glycol, glycerol, trimethylol propane, pentaerythritol and 1,4-cyclohexane dimethanol. The polyglycidyl ethers can also be derived from polymeric polyols such as polypropylene glycol, polyurethane polyols, and polyesters polyols.

Polyglycidyl esters of polycarboxylic acid can be formed by reacting epichlorohydrin or another epoxy material with an aliphatic or aromatic polycarboxylic acid such as succinic acid, adipic acid, azelaic acid, sebacic acid, maleic acid, 2,6-naphthalene dicarboxylic acid, fumaric acid, phthalic acid, tetrahydrophthalic acid, hexahydrophthalic acid, or trimellitic acid. Polyglycidyl esters of polycarboxylic acids can also be formed from dimerized unsaturated fatty acids containing about 36 carbon atoms.

Suitable epoxy resins also include epoxy novolac resins. Epoxy novolac resins can be obtained by reacting an epihalohydrin with the condensation product of aldehyde and monohydric or polyhydric phenols.

The compositions used in the process of the invention also contain a source of active hydrogen that will react with the isocyanate that is generated when exposing the uretidione or polyuretidione to UV radiation in the 100-315 nm range. The active hydrogen can be selected from primary amine, secondary amine, thiol and/or hydroxyl with hydroxyl being preferred.

As mentioned above the uretidione obtained from the dimerization of a diisocyanate can be further reacted with an active hydrogen-containing compound having a functionality of 2 or more for examples polyols. By using excess polyol a hydroxyl uretidione or polyuretidione can be obtained.

Alternatively active hydrogens can be present as a separate ingredient. Examples of active hydrogen-containing materials that can be present as a separate ingredient are polyester polyols, hydroxyl-containing (meth)acrylic polymers and polyurethane polyols.

Suitable polyester polyols can be prepared by the polyesterification of an organic polycarboxylic acid or anhydride thereof with organic polyols and/or an epoxide as is well known in the art.

Suitable organic polycarboxylic acids include carboxylic acids or anhydrides. The following acids can be used: phthalic acid, isophthalic acid, terephthalic acid, tetrahydrophthalic acid, hexahydrophthalic acid, adipic acid, azelaic acid, sebacic acid, maleic acid, glutaric acid, chlorendic acid, tetrachlorophthalic acid, and other dicarboxylic acids of varying types. Minor amounts of monobasic acids such as benzoic acid, stearic acid, acetic acid, hydroxystearic acid and oleic acid can be included. Higher polycarboxylic acids such as trimellitic acid and tricarballylic acid can also be used.

It is understood that anhydrides of the abovementioned acids can be used in place of the acids. Lower alkyl esters of the acids such as dimethyl glutarate and dimethyl terephthalate can also be used in place of the acid.

Suitable organic polyols include the following diols: alkylene glycols such as ethylene glycol, neopentyl glycol, other glycols such as hydrogenated bisphenol A, cyclohexanediol, cyclohexanedimethanol, caprolactonediol, hydroxyalkylated bisphenols, polyether glycols. Suitable organic polyols also include polyols of higher functionality like trimethylolpropane, trimethylolethane, and pentaerythritol as well as high molecular weight polyols. High molecular weight polyols can be produced by oxyalkylating low molecular weight polyols.

Suitable hydroxy-containing (meth)acrylic polymers include polymers of hydroxy-containing vinyl monomers such as hydroxyalkyl (meth)acrylate and other ethylenically unsaturated copolymerizable materials such as alkyl (meth) acrylates. The hydroxyalkyl (meth)acrylates can be acrylic acid and methacrylic acid esters of ethylene glycol and propylene glycol, hydroxy-containing esters and/or amides of unsaturated acids such as maleic acid, fumaric acid, and itaconic acid. The alkyl (meth)acrylates can be lauryl methacrylate, 2-ethylhexyl methacrylate, and n-butyl acrylate.

Suitable hydroxy-containing (meth)acrylic polymers can be formed from the copolymerization of ethylenically unsaturated monomers such as monoolefinic and diolefinic hydrocarbons, halogenated monoolefinic and diolefinic hydrocarbons, unsaturated esters of organic and inorganic acids, amides and esters of unsaturated acids, nitriles, and unsaturated acids. Unsaturated acids can also be copolymerized with hydroxyalkyl (meth)acrylates. Examples of the ethylenically unsaturated monomers include styrene, 1,3-butadiene, acrylamide, acrylonitrile, alpha-methyl styrene, alpha-methyl chlorostyrene, vinyl butyrate, vinyl acetate, allyl chloride, divinyl benzene, diallyl itaconate, triallyl cyanurate, and mixtures thereof. The ethylenically unsaturated materials can be used in admixture with the above-mentioned acrylates and methacrylates.

Examples of polyurethane polyols are those that can be prepared by reacting polyols with a polyisocyanate (OH/NCO equivalent ratio greater than 1:1) as are well known in the art. Suitable polyols include diols and triols such as aliphatic polyols, for example, alkylene polyols containing from 2 to 18 carbon atoms. Other suitable diols include ethylene glycol, 1,4-butanediol, 1,6-hexanediol, cycloaliphatic polyols such as 1,2-hexanediol, and cyclohexanedimethanol. Other suitable triols include trimethylolpropane and trimethylolethane. Polyols containing ether linkages such as diethylene glycol and triethylene glycol can also be used. Also, acid-containing polyols such as dimethylolpropionic acid can be used. Besides monomeric polyols polymeric polyols such as the polyester polyols and hydroxyl-containing (meth)acrylic polymers, such as those mentioned above can be used, typically in combination with the monomeric polyols.

The polyisocyanate can be an aliphatic or an aromatic isocyanate or a mixture of the two such as those mentioned above.

The uretidione content is typically present in the curable composition in an amount ranging from 5 to 90 or from 7 to 50 or from 10 to 30, weight percent based on the total weight of the reactants used in forming the curable composition.

The active hydrogen content is typically present in the curable composition in an amount ranging from 5 to 50 or 10 to 30 weight percent based on total weight of the reactants used in forming the curable composition.

As used herein the term "polythiol functional material" refers to polyfunctional materials containing two or more thiol functional groups (SH). Suitable polythiol functional materials for use in the curable compositions are numerous and can vary widely. Non-limiting examples of suitable polythiol functional materials can include, but are not limited to, polythiols having at least two thiol groups including compounds and polymers. The polythiol can have ether linkages (—O—), sulfide linkages (—S—), including polysulfide linkages (—$S_x$—), wherein x is at least 2, such as from 2 to 4, and combinations of such linkages.

The polythiols for use in the present invention include, but are not limited to, materials of the formula:

wherein $R_1$ is a polyvalent organic moiety including monomer and polymeric moiety and n is an integer of at least 2, typically 2 to 6.

Non-limiting examples of suitable polythiols include, but are not limited to, esters of thiol-containing acids of the formula HS—$R_2$—COOH wherein $R_2$ is an organic moiety with polyhydroxy compounds of the structure $R_3$—$(OH)_n$ wherein R₃ is an organic moiety and n is at least 2, typically 2 to 6. These components can be reacted under suitable conditions to give polythiols having the general structure:

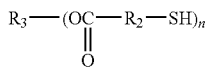

wherein R₂, R₃ and n are as defined above.

Examples of thiol-containing acids are thioglycolic acid (HS—CH₂COOH), α-mercaptopropionic acid (HS—CH(CH₃)—COOH) and β-mercaptopropionic acid (HS—CH₂CH₂COCH) with polyhydroxy compounds such as glycols, triols, tetraols, pentaols, hexaols, and mixtures thereof. Other non-limiting examples of suitable polythiols include, but are not limited to, ethylene glycol bis(thioglycolate), ethylene glycol bis(β-mercaptopropionate), trimethylolpropane tris(thioglycolate), trimethylolpropane tris(β-mercaptopropionate), pentaerythritol tetrakis(thioglycolate) and pentaerythritol tetrakis(β-mercaptopropionate), and mixtures thereof.

The polythiol can be a monomeric material having a molecular weight less than 550 such as those described above or a polymeric material having a molecular weight greater than 700. The molecular weight is an actual molecular weight for monomeric materials and is on a number average bases for the polymeric materials.

The polymeric polythiols have a polymer or resin backcone for example a polyether resin, polyester resin, polyurethane resin, a polycarbonate resin or polyacrylate resin, resin backbone. Such materials are typically prepared by reacting a hydroxyl-functional polymer or resin with thiol-containing acids as described above. Alternatively, acid functional resin or polymers may be further reacted with a mercapto alcohol such as mercapto ethanol.

For the polyether resin backbone, any suitable polyalkylene ether polyol may be used. Included are poly(oxytetramethylene)glycols, poly(oxyethylene)glycols, polypropylene glycols and the reaction product of ethylene glycol with a mixture of propylene oxide and ethylene oxide.

Also useful are polyether polyols formed from the oxyalkylation of various polyols, for example, glycols such as ethylene glycol, 1,6-hexanediol, Bisphenol A, and the like, or higher polyols, such as trimethylol propane, pentaerythritol and the like. One commonly utilized oxyalkylation method is by reacting a polyol with an alkylene oxide, for example, ethylene or propylene oxide, in the presence of an acidic or basic catalyst.

Polyester polyols can also be used as a polymeric polyol. The polyester polyols can be prepared by the polyesterification of organic polycarboxylic acids or anhydrides thereof with organic polyols. Usually, the polycarboxylic acids and polyols are aliphatic or aromatic dibasic acids and diols.

The diols which are usually employed in making the polyester include alkylene glycols, such as ethylene glycol and butylene glycol, neopentyl glycol and other glycols such as hydrogenated Bisphenol A, cyclohexane diol, cyclohexane dimethanol, caprolactone diol (for example, the reaction product of caprolactone and ethylene glycol), hydroxyalkylated bisphenols, polyether glycols, for example, poly(oxytetramethylene)glycol and the like. However, other diols of various types and, as indicated, polyols of higher functionality can also be utilized. Such higher polyols can include, for example, trimethylol propane, trimethylol ethane, pentaerythritol, and the like, as well as higher molecular weight polyols such as those produced by oxyalkylating low molecular weight polyols. An example of such high molecular weight polyol is the reaction product of 20 moles of ethylene oxide per mole of trimethylol propane.

The acid component of the polyester consists primarily of monomeric carboxylic acids or anhydrides having 2 to 18 carbon atoms per molecule. Among the acids which are useful are phthalic acid, isophthalic acid, terephthalic acid, tetrahydrophthalic acid, hexahydrophthalic acid, adipic acid, azelaic acid, sebacic acid, maleic acid, glutaric acid, chlorendic acid, tetrachlorophthalic acid and other dicarboxylic acids of varying types. Also, there may be employed higher polycarboxylic acids such as trimellitic acid and tricarballylic acid (where acids are referred to above, it is understood that the anhydrides of those acids which form anhydrides can be used in place of the acid). Also, lower alkyl esters of acids such as dimethyl glutarate can be used.

Besides polyester polyols formed from polybasic acids and polyols, polycaprolactone-type polyesters can also be employed. These products are formed from the reaction of a cyclic lactone such as epsilon-caprolactone with a polyol with primary hydroxyls such as those mentioned above. Such products are described in U.S. Pat. No. 3,169,949 to Hostettler.

In addition to the polyether and polyester polyols, hydroxy-containing (meth)acrylic polymers or (meth)acrylic polyols can be used as the polyol component.

Among the (meth)acrylic polymers are polymers of about 2 to 20 percent by weight hydroxy-containing vinyl monomers such as hydroxyalkyl (meth)acrylate having 2 to 6 carbon atoms in the alkyl group and 80 to 98 percent by weight of other ethylenically unsaturated copolymerizable materials such as alkyl (meth)acrylates; the percentages by weight being based on the total weight of the monomeric charge.

Examples of suitable hydroxyalkyl(meth)acrylates are hydroxy ethyl, hydroxy propyl and hydroxy butyl(meth)acrylate.

Examples of suitable alkyl(meth)acrylates are lauryl methacrylate, 2-ethylhexyl methacrylate and n-butyl acrylate.

Besides the acrylates and methacrylates, other copolymerizable monomers which can be copolymerized with the hydroxyalkyl(meth)acrylates are ethylenically unsaturated materials such as monoolefinic and diolefinic hydrocarbons, halogenated monoolefinic and diolefinic hydrocarbons, unsaturated esters of organic and inorganic acids, amides and esters of unsaturated acids, nitriles and unsaturated acids and the like. Examples of such monomers include styrene, 1,3-butadiene, acrylamide, acrylonitrile, alpha-methyl styrene, alpha-methyl chlorostyrene, vinyl butyrate, vinyl acetate, allyl chloride, divinyl benzene, diallyl itaconate, triallyl cyanurate and mixtures thereof. Usually these other ethylenically unsaturated materials are used in admixture with the above-mentioned acrylates and methacrylates.

In addition to the polymeric polyols mentioned above, polyurethane polyols can also be used. These polyols can be prepared by reacting any of the above-mentioned polyols with a minor amount of polyisocyanate (OH/NCO equivalent ratio greater than 1:1) so that free primary hydroxyl groups are present in the product. In addition to the high molecular weight polyols mentioned above, mixtures of both high molecular weight and low molecular weight polyols such as those mentioned above may be used.

The organic isocyanate which is used to prepare the polyurethane polyols can be an (cyclo)aliphatic or an aromatic isocyanate or a mixture of the two. (Cyclo)aliphatic isocyanates are preferred. Also, diisocyanates are preferred although higher polyisocyanates and can be used in place of or in combination with diisocyanates. Examples of suitable higher polyisocyanates are 1,2,4-benzene triisocyanate and polymethylene polyphenyl isocyanate. Examples of suitable aromatic diisocyanates are 4,4'-diphenylmethane diisocyanate, 1,3-phenylene diisocyanate, 1,4-phenylene diisocyanate and toluene diisocyanate. Examples of suitable (cyclo)aliphatic diisocyanates are straight chain aliphatic diisocyanates such as 1,4-tetramethylene diisocyanate and 1,6-hexamethylene diisocyanate. Also, cycloaliphatic diisocyanates can be employed. Examples include 1,4-cyclohexyl diisocyanate, isophorone diisocyanate, alpha, alpha-xylylene diisocyanate and 4,4'-methylene-bis-(cyclohexyl isocyanate).

The photoactivable bases useful in the practice of the invention are known in the art. Preferred materials are those that generate a strong base such as an amidine base such as the bicyclic amidines particularly 1,8-diazobicyclo[5.4.0]undec-7-ene ("DBN"); 1,5-diazobicyclo[4.3.0]non-5-ene ("DBU"); and tetramethylguanidine ("TMG"). Such compounds are described in U.S. 2004/0242867.

Preferred photoactivable bases are those based on aryl-substituted diazobicyclic compounds, such as those of the structure

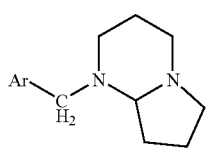

where Ar is an aromatic group such a phenyl and substituted phenyl such as

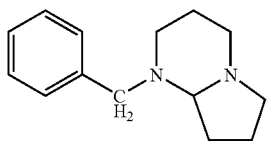 [SMILES: c1ccc(CN2CCCN3CCCC32)cc1]

that generate DBN

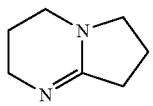

upon exposure to UV radiation as described above.

The relative amounts of the polyuretidione and the polythiol can vary depending somewhat on their respective molecular weights. Typically, they can each be present in amounts within the range of 10 to 90% by weight based on resin solids weight of the polyuretidione and polythiol. The equivalent ratio of thiol to uretidione is typically from 0.5 to 1.5:1.

The photoactivable base is typically present in amounts of 0.5 to 5% by weight based on resin solids weight of the polyuretidione and polythiol.

The compositions used in the invention can also comprise photoinitiators or photosensitizers. Depending on the type of materials used in the composition, free radical photoinitiators or photosensitizers and/or cationic photoinitiators can be included.

Examples of suitable free radical photoinitiators include benzoin and benzoin derivatives. Examples of benzoin derivatives are benzoin ethers such as isobutyl benzoin ether and benzyl ketals such as benzyl dimethyl ketal, 2-hydroxy-2-methyl-1-phenylpropan-1-one and 4-(2-hydroxyethoxy) phenyl-2-hydroxy-2-propyl ketone. Acyl phosphines such as 2,4,6-trimethylbenzoyl diphenylphosphine oxide and bis(2,4,6-trimethylbenzoyl)phenylphosphine oxide can also be used as free radical photoinitiators. Further, aryl ketones such as 1-hydroxycyclohexyl phenyl ketone, 2-benzyl-2-dimethylamino-1-(4-morpholinophenyl)-butan-1-one, 2,2-dimethoxy-2-phenylaceto-phenone, and 2-methyl-1-(4-(methylthiophenyl)-2-(4-morphorlinyl))-1-propanone can be used as free radical photoinitiators.

Suitable cationic photoinitiators include diaryliodonium salts with copper synergist such as diphenyl iodonium hexafluorophosphate, dibenzyl iodonium hexaflouroarsinate, and copper acetate; triarylsulfonium salts such as triphenyl sulphonium hexafluorophosphate; and triphenyl sulphonium tertafluoroborate. Dialkylphenacyl-sulfonium salts, ferrocenium salts such as cyclopentadienyl iron(II) hexafluorophosphate, alpha-sulfonyloxy ketone, and silyl benzyl ethers can also be used.

Examples of photosensitizers include aromatic ketones, such as substituted or unsubstituted benzophenones, thioxanthones and anthraquinones.

Examples of suitable benzophenones and thioxanthones are benzophenone, 4,4'-bis(dimethylamino)benzophenone, 4,4'-bis(diethylamino)benzophenone, 4,4'-bis(ethylmethylamino)benzophenone, 4,4'-diphenylbenzophenone, 4,4'-diphenoxybenzophenone, 4,4'-bis(p-isopropylphenoxy) benzophenone, 4-methylbenzophenone, 2,4,6-trimethylbenzophenone, 4-phenylbenzophenone, 2-methoxycarbonyl-benzophenone, 4-(4-methylphenylthio)benzophenone, 4-methoxy-3,3'-methylbenzophenone, isopropylthioxanthone, chlorothioxanthone, 1-chloro-4-propoxythioxanthone, 2,4-dimethylthioxanthone, 2,4-diethylthioxanthone, 1,3-dimethyl-2-(2-ethylhexyloxy)thioxanthone.

Likewise mixtures of photosensitizers can be used, for example, a mixture of benzophenone and isopropylthioxanthone.

The photoinitiators or photosensitizers are present in amounts of 0.01 to 10, such as 0.5 to 2% based on solids weight of the composition.

In addition to the polyuretidiones and polythiols, the composition may also include other binders, such as olefinically unsaturated compounds. The unsaturated compounds may include one or more olefinically double bonds. They may be of low molecular weight (monomeric) or higher molecular weight (polymeric).

Examples of monomers having two or more double bonds are the diacrylates of ethylene glycol, propylene glycol, neopentyl glycol, hexamethylene glycol, bisphenol A, trimethylolpropane triacrylate, pentaerythritol triacrylate or tetraacrylate, vinyl acrylate, divinyl benzene, divinyl succinate, diallyl phthalate, triallyl phosphate, triallyl isocyanurate and tris(2-acryloylethyl)isocyanurate.

Examples of polyunsaturated compounds of relatively high molecular weight are acrylated epoxy resins, acrylated polyesters or polyesters containing vinyl ether groups or epoxy groups. Further examples of unsaturated polymers are unsaturated polyester resins which are mostly prepared from maleic acid, and one or more diols and have number average molecular weights of from about 500 to 3000. In addition it is also possible to employ vinyl ether monomers and oligomers, and also maleate-terminated oligomers with polyester, polyurethane, polyether, polyvinyl ether and epoxy main chains.

The other binders when present are present in amounts of up to 50% more typically 10 to 40% by weight based on weight of resin solids.

The compositions of the invention are cured by subjecting the compositions to UV radiation.

The wave length of the UV radiation generally extends from about 100 nanometer (nm) through the UV region. Typically, the wave length range is from 100-650 nm. Suitable radiation comprises light from artificial sources. Therefore, a large number of very different types of light source can be used. Both point sources and flat radiators (lamp carpets) are suitable. Examples are carbon arc lamps, xenon arc lamps, medium-pressure, high-pressure and low pressure mercury lamps, doped if desired with metal halides (metal halogen lamps), microwave-stimulated metal vapour lamps, excimer lamps, superactinic fluorescent tubes, fluorescent lamps, incandescent argon lamps, electronic flashlights, xenon flashlights, photographic flood lamps, electron beams and X-rays, produced by means of synchrotrons or laser plasma. The distance between the lamp and the substrate according to the invention which is to be exposed can vary depending on the application and on the type and/or power of the lamp, for example between 2 cm and 150 cm such as 10 to 25 cm. The duration of radiation is in the region of a few seconds for example within the range of 35 seconds to 400 seconds such as 5 seconds to 160 seconds.

For the generation of isocyanate groups from the uretidiones, the uretidione composition typically in the form of a coating layer is exposed to high-energy radiation in the wavelength range 100 to 315 nm. Examples of such UV radiation sources are optionally doped high-pressure, medium-pressure and low-pressure mercury vapour radiators, gas discharge tubes such as, for example, low-pressure xenon lamps, pulsed and unpulsed TV lasers, UV spot radiators such as, for example, UV-emitting diodes and black light tubes. So-called high-energy electron flash devices (UV flash lamps) can be used as the radiation source.

The UV radiation source typically delivers energy at a level of 200 to 2000 Joules.

The distance of the UV source from the substrate surface to be irradiated may be from 2 to 150 cm, such as 10 to 25 cm.

The duration of irradiation is in the region of a few seconds, for example within the range 3 seconds to 400 seconds, such as 5 to 160 seconds.

Depending on the light source used it is advantageous in many cases to employ a sensitizer, as described above, whose absorption spectrum coincides as closely as possible to the emission spectrum of the radiation source.

In addition to the ingredients mentioned above the compositions above may contain various optional ingredients. Examples of these are fillers and reinforcing agents, for example calcium carbonate, silicates, talc, kaolin, mica and barium sulfate. Other additives, for example plasticizers, lubricants and rheological additives and solvent or diluent may be included in the compositions. When present these optional ingredients may constitute up to 50% by weight of the composition based on total weight of the composition.

The compositions of the present invention also contain a colorant. As used herein, the term "colorant" means any substance that imparts color and/or other opacity and/or other visual effect to the composition. The colorant can be added to the coating in any suitable form, such as discrete particles, dispersions, solutions and/or flakes. A single colorant or a mixture of two or more colorants can be used in the coatings of the present invention.

Example colorants include pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coatings by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DP-PBO red"), titanium dioxide, carbon black and mixtures thereof. The terms "pigment" and "colored filler" can be used interchangeably.

Example dyes include, but are not limited to, those that are solvent and/or aqueous based such as phthalo green or blue, iron oxide, bismuth vanadate, anthraquinone, perylene, aluminum and quinacridone.

Example tints include, but are not limited to, pigments dispersed in water-based or water miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemical, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800 B2, which is incorporated herein by reference. Nanoparticle dispersions can also be produced by crystallization, precipitation, gas phase condensation, and chemical attrition (i.e., partial dissolution). In order to minimize re-agglomeration of nanoparticles within the coating, a dispersion of resin-coated nanoparticles can be used. As used herein, a "dispersion of resin-coated nanoparticles" refers to a continuous phase in which is dispersed discreet "composite microparticles" that comprise a nanoparticle and a resin coating on the nanoparticle. Example dispersions of resin-coated nanoparticles and methods for making them are identified in United States Patent Application Publication 2005-0287348 A1, filed Jun. 24, 2004, U.S. Provisional Application No. 60/482,167 filed Jun. 24, 2003, and U.S. patent application Ser. No. 11/337,062, filed Jan. 20, 2006, which is also incorporated herein by reference.

Example special effect compositions that may be used in the compositions of the present invention include pigments and/or compositions that produce one or more appearance effects such as reflectance, pearlescence, metallic sheen, phosphorescence, fluorescence, photochromism, photosensitivity, thermochromism, goniochromism and/or color-change. Additional special effect compositions can provide other perceptible properties, such as opacity or texture. In a non-limiting embodiment, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

In general, the colorant can be present in any amount sufficient to impart the desired visual and/or color effect. The colorant may comprise from 1 to 65 weight percent of the present compositions, such as from 3 to 40 weight percent or 5 to 35 weight percent, with weight percent based on the total weight of the compositions.

The compositions are stable at ambient temperature and the ingredients can be formulated into one pack (package) system. Alternately, the component can be separated into a 2 or 3 pack system and the packages combined before application.

The compositions of the invention can be employed for various purposes, for example as printing inks and as coatings for paper, wood, metal or plastic.

Of particular interest is the use of the compositions of the invention for preparing protective and decorative coatings, such as exterior coatings on substrates of all kinds, for example buildings, fences, chipboard panels, and as a coating on stone, concrete or metal, for the coating of vehicles, for example, such as cars, railways or aircraft. The compositions may likewise be used in automotive OEM finishing and automotive refinish, and also for the finishing of car bodies, plastic parts for cars and body-mounted car parts. The initiators of the invention can be used in a multicoat system in the surfacer, base coat or clearcoat. Their use in pigmented topcoats is also possible.

The substrates can be coated by applying the composition as a liquid that may be 100% solids composition or as a solution or dispersion to the substrate. The choice of solvent or diluent and the concentration depend predominantly on the type of composition and the coating process. The solvent or diluent should be inert. In other words, it should not undergo any chemical reaction with the components and should be capable of being removed after the coating operation in the curing process. Examples of suitable solvents or diluents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solvent or diluent is typically present in the compositions in amounts of 0 to 30% by weight based on total weight of the composition.

Using known coating processes, the coating composition may be applied uniformly to a substrate, for example by spin coating, dip coating, knife coating, curtain coating, brushing, spraying, especially electrostatic spraying and reverse roll coating.

The coating thickness after curing is typically from 0.5 to 125, such as 0.5 to 100 microns.

EXAMPLES

The following examples are intended to illustrate the invention and should not be construed as limiting the invention in any way. All parts and percentages are by weight unless otherwise indicated.

Example 1

| Ingredient | Formula A Total Mass | Formula B Total Mass | Formula C Total Mass |
|---|---|---|---|
| Trimethylolpropane mercaptopropionate[1] | 21.0 | 20.9 | 20.8 |
| HDI Polyuretidione[2] | 79.0 | 78.6 | 78.2 |
| CGI-90[3] | 0.0 | 0.5 | 0.5 |
| DAROCUR ITX[4] | — | — | 0.5 |
| | 100.00 | 100.00 | 100.00 |

[1]Thiol compound from Sigma Aldrich.
[2]Polyuretidione from Bayer Material Science, Inc. prepared from Desmodur N3400, 2-ethylhexanol and 2-ethyl-1,3-hexanediol; the solids was 50% in n-butyl acetate; the uretidione equivalent weight as supplied was 1341.
[3]Photo-latent catalyst from CIBA Specialty Chemicals Corporation - blocked DBN (1,5-diazabicyclo[4.3.0]non-5-ene) supplied at 100% weight solids.
[4]Photoinitiator synergist from CIBA Specialty Chemicals Corporation Isopropyl-9H-thioxanthen-9-one supplied at 100% weight solids.

The coating compositions of Example 1 were diluted to between 53.0 to 55.0% weight solids by the addition of n-butyl acetate solvent. The compositions were applied using a #8 square draw down bar on pre-coated E-Coat 6061 primed cold rolled steel panels available from ACT Test Panels, Inc. of Hillsdale, Mich. The coatings were flashed for 30 minutes at ambient temperature. The coatings were then irradiated using 2 passes under two medium pressure mercury vapor lamp housed in a laboratory RPC UV Processor available from PRC Industries, Inc, Plainfield, Ill. The conveyor speed was 20 fpm. Lamp distance from the coated surface was 8 inches. The UV "dose" measured by a dosemeter (photocell) ranged from 940 to 1035 millijoules/cm$^2$ per pass. Infrared analysis showed some disappearance of a characteristic uretidione peak at 1764 cm−1 indicative of a photo-latent catalyst reaction and a subsequent uretidione reaction in formulas B and C. Surface tack and gellation were also evidence of a reaction (cure response) in the formulas containing photo-latent catalyst. Coatings were tested after UV irradiation plus 24 hours at ambient temperature. The results are reported in the table below.

| EXAMPLE 1 | Infrared Absorbance at 1764 cm−1 | Surface Tack[1] (UV + 24 hours Ambient) | MEK Double Rubs[2] (UV + 24 hours Ambient) |
|---|---|---|---|
| Formula A | 0.33 | No cure | No Cure |
| Formula B | 0.22 | Moderately tacky | 10-20 |
| Formula C | 0.15 | Moderately tacky | 50-80 |

[1]ASTM D2377-00 (2006)
[2]ASTM D4752

Example A

This example illustrates the preparation of the reaction product of the trimer of hexamethylene diisocyanate and 2-ethyl hexanol.

A reaction vessel equipped stirrer, thermocouple, condenser and an addition funnel was charged with 274.2 grams (g) of n-butyl acetate, 164.0 g Desmodur N3300 and 0.55 g of 10% solution of dibutyltin dilaurate in n-butyl acetate and heated to 75° C. Then 110.7 g 2-ethyl hexanol was gradually added to the vessel over a period of 15 minutes during which time the reaction temperature increased to 92° C. The reactions contents were allowed to cool to 80° C. and then stirred until no isocyanate (2264 cm−1) was observed by infrared spectroscopy. Thereafter, heating was discontinued, the contents of the vessel were allowed to cool.

The resultant product had a total solids content measured for 1 hour at 110° C. of 50.2 percent by weight; had a peak molecular weight of 1224, a weight average molecular weight of 1854 and a number average molecular weight of 1342 as determined by gel permeation chromatography utilizing a polystyrene standard; had a Brookfield viscosity of 24 centipoise; had a weight/gallon of 7.99.

Example B

This example illustrates the preparation of the reaction product of the trimer of isophorone diisocyanate and 2-ethyl hexanol.

A reaction vessel equipped stirrer, thermocouple, condenser and an addition funnel was charged with 182.2 grams (g) of n-butyl acetate, 277.8 g Desmodur Z4470 and 0.53 g of 10% solution of dibutyltin dilaurate in n-butyl acetate and heated to 75° C. Then 102.6 g 2-ethyl hexanol was gradually added to the vessel over a period of 15 minutes during which time the reaction temperature increased to 81° C. The reaction contents were heated to 85° C. and then stirred until no isocyanate (2264 cm−1) was observed by infrared spectroscopy. Thereafter, heating was discontinued, the contents of the vessel were allowed to cool.

The resultant product had a total solids content measured for 1 hour at 110° C. of 53.8 percent by weight; had a peak molecular weight of 1115, a weight average molecular weight of 1460 and a number average molecular weight of 1201 as determined by gel permeation chromatography utilizing a polystyrene standard; had a Brookfield viscosity of 58 centipoise; had a weight/gallon of 8.06.

Examples 2 and Comparative Examples 3 and 4

Samples of Vestagon BF1320, Example A and Example B were drawn down on glass plates. The plates were irradiated using a laboratory RPC UV Processor available from PRC Industries, Inc, Plainfield, Ill. The conveyor speed was 20 fpm. Lamp distance from the coated surface was 8 inches. The UV "dose" measured by a dosemeter (photocell referred to as UV-Power Puck) equaled 973 millijoules/cm$^2$ per pass.

FTIR spectra showed a typical isocyanate peak for the Vestagon BF1320 sample but not for Example A and B. The isocyanate concentration was quantified by titration.

| Sample | NCO Equiv. Wt. |
|---|---|
| Vestagon BF1320 + 1 pass UV | 5463 (as is)<br>4866 (100%) |
| Example A + 1 pass UV | 19,800 (as is) |
| Example B + 1 pass UV | >40,000 (as is) |

Examples 5 (Comparative) and 6, 7

Samples of Vestagon BF1320 (Polyuretidione from Degussa Corporation), 40% solids in 50/50 methly isobutyl ketone/n-butyl acetate, were drawn down on glass plates. The plates were irradiated using a laboratory RPC UV Processor available from PRC Industries, Inc, Plainfield, Ill. The conveyor speed was 20 fpm. Lamp distance from the coated surface was 8 inches. The UV "dose"[1] measured by a dosemeter (photocell referred to as UV-Power Puck) equaled 973 millijoules/cm$^2$ per pass. FTIR spectra showed typical isocyanate peaks. These peaks were not evident prior to the irradiation. The isocyanate was quantified by titration.

[1] UV DOSE is the total ampunt of radiant energy exposed at the surface and is dependent upon (1) the time of exposure, (2) the number of exposures to the light source, and (3) the radiant power. Dose is expressed in Joules or millijoules.

| Sample | Dosage (mJ/cm$^2$) | NCO Equiv. Wt. (based 100% solids) | % Change in NCO EW |
|---|---|---|---|
| Vestagon BF1320 | — | 16875 | — |
| Vestagon BF1320 + 1 pass UV | 986 | 11260 | 33 |
| Vestagon BF1320 + 2 passes UV | 1950 | 5620 | 67 |

What is claimed:

1. A curable composition comprising
   (a) a polyuretidione that contains from 5 to 45% by weight of uretidione groups; 10 to 55% by weight of urethane groups; and less than 2% by weight of isocyanate groups, the percentages by weight being based on total weight of uretidione, urethane and isocyanate groups;
   (b) a polythiol; and
   (c) a photoactivable nitrogen containing base.

2. The composition of claim 1 in which the polyuretidione contains at least 2 uretidione groups.

3. The composition of claim 1 in which the polyuretidione contains from 2 to 10 uretidione groups.

4. The composition of claim 1 in which the polyuretidione is prepared by reacting a polyisocyanate containing 1 or more uretidione groups with at least one polyol and optionally a blocking agent for isocyanate.

5. The composition of claim 4 in which the polyisocyanate contains from 4 to 20 carbon atoms.

6. The composition of claim 5 in which the polyisocyanate is a (cyclo) aliphatic polyisocyanate.

7. The composition of claim 6 in which the polyisocyanate is a diisocyanate.

8. The composition of claim 7 in which the diisocyanate is isophorone diisocyanate.

9. The composition of claim 1 in which the polythiol is a monomeric polythiol having a molecular weight less than 550.

10. The composition of claim 1 in which the polythiol is a polymeric polythiol having a number average molecular weight greater than 700.

11. The composition of claim 1 in which the photoactivable nitrogen containing base upon exposure to ultraviolet light generates an amidine base.

12. The composition of claim 11, in which the amidine base is selected from 1,8-diazobicyclo[5.4.0]undec-7-ene, 1,5-diazobicyclo[4.3.0]non-5-ene and tetramethylguanidine.

13. The composition of claim 11 in which the photoactivable nitrogen containing base has the following structure:

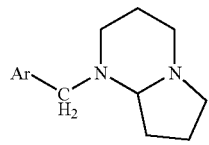

where Ar is an aromatic moiety.

14. The composition of claim 13 where Ar is a phenyl including a substituted phenyl moiety.

15. The composition of claim 1 in which the equivalent ratio of thiol to uretidione is from 0.5 to 1.5:1.

16. The composition of claim 1 in which the photoactivable nitrogen containing base is present in amounts from 0.5 to 5% by weight of resin solids of (a) and (b).

17. The composition of claim 1 which additionally contains a photo-sensitizer.

18. The composition of claim 17 in which the photosensitizer is present in amounts of 0.5-2 weight % based on weight of polyuretidione, polythiol, photoactivable nitrogen containing base and photosensitizer.

19. The composition of claim 17 in which the photosensitizer is selected from a benzophenone, and a thioxanthrone.

\* \* \* \* \*